United States Patent [19]

Villani et al.

[11] Patent Number: 4,659,716

[45] Date of Patent: Apr. 21, 1987

[54] ANTIHISTAMINIC 8-(HALO)-SUBSTITUTED 6,11-DIHYDRO-11-(4-PIPERIDYLIDENE)-5H-BENZO[5,6]CYCLOHEPTA[1,2-b]PYRIDINES

[75] Inventors: Frank J. Villani, Fairfield; Jesse K. Wong, Union, both of N.J.

[73] Assignee: Schering Corporation, Madison, N.J.

[21] Appl. No.: 838,974

[22] Filed: Mar. 12, 1986

Related U.S. Application Data

[63] Continuation-in-part of Ser. No. 580,304, Feb. 15, 1984, abandoned.

[51] Int. Cl.[4] .................. A61K 31/445; C07D 401/08
[52] U.S. Cl. ......................................... 514/290; 546/93
[58] Field of Search ........................... 546/93; 514/290

[56] References Cited

U.S. PATENT DOCUMENTS

| | | | |
|---|---|---|---|
| 3,326,924 | 6/1967 | Villani | 546/93 |
| 3,717,647 | 2/1973 | Villani | 546/315 |
| 4,282,233 | 8/1981 | Villani | 546/93 X |

FOREIGN PATENT DOCUMENTS

46-20387  6/1971  Japan ...................................... 546/93

OTHER PUBLICATIONS

PDR, 1984, pp. 515, 529, 557, 558, 566, 593, 594, 611, 631, 633, 648, 664, 667, 668, 709.
Scrip No. 1026, 8/19/85.
*Burger's Medicinal Chemistry,* 4th Ed, Part III, Wiley-Interscience, NY, 1981, pp. 818-819.
Brandon, M., et al., *Annals of Allergy,* 44, 71-75 (1980).
Business Week, 5/2/83, pp. 60-61.
Villani, F., et al., *Arzneim.-Forsch.,* 36(11), Nr. 9 1986, pp. 1311-1314.
Villani, F. et al., *J. Med. Chem.,* 15(7), 750-754 (1972).
Goodman and Gilman's, *The Pharmacological Basis of Therapeutics,* MacMillan, New York, 1980, p. 626.
PDR, 1985, pp. 888, 889, 964, 1425, 1426, 1485, 1612, 1613, 1725, 1726, 1872, 1873, 1879, 1965, 1966, 2276, 2277.

*Primary Examiner*—Richard A. Schwartz
*Attorney, Agent, or Firm*—James R. Nelson; Stephen I. Miller; Richard C. Billups

[57] ABSTRACT

Disclosed are 7- and/or 8-(halo or trifluoromethyl)-substituted-6,11-dihydro-11-(4-piperidylidene)-5H-benzo[5,6]cyclohepta[1,2-b]pyridines and the pharmaceutically acceptable salts thereof, which possess antihistaminic properties with substantially no sedative properties. Methods for preparing and using the compounds and salts are described.

16 Claims, No Drawings

4,659,716

ANTIHISTAMINIC 8-(HALO)-SUBSTITUTED 6,11-DIHYDRO-11-(4-PIPERIDYLIDENE)-5H-BENZO[5,6]CYCLOHEPTA[1,2-B]PYRIDINES

The present application is a continuation-in-part of U.S. application Ser. No. 580,304, filed Feb. 15, 1984, now abandoned, the benefit of which is claimed pursuant to the provisions of 35 U.S.C. 120.

BACKGROUND OF THE INVENTION

U.S. Pat. Nos. 3,326,924, 3,717,647 and 4,282,233 describe certain 11-(4-piperidylidene)-5H-benzo[5,6]cyclohepta[1,2-b]pyridines.

SUMMARY OF THE INVENTION

The present invention is directed to compounds having structural formula I:

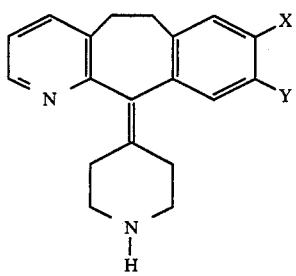

or pharmaceutically acceptable salts thereof, wherein X and Y independently represent H, halo (i.e., fluoro, chloro, bromo or iodo), or trifluoromethyl with the proviso that at least one of X and Y is halo or trifluoromethyl. Particularly, preferred compounds are those wherein X is F and Y is H and wherein X is Cl and Y is H.

The compounds of the invention have unexpectedly been found to possess advantageous antihistaminic activity and low central nervous system (CNS) activity indicative of non-sedation. The compounds can thus be employed in pharmaceutical compositions in combination with pharmaceutically acceptable carriers and in methods of treating allergic reactions in a mammal.

DESCRIPTION OF THE INVENTION

The compounds of the invention can form salts with pharmaceutically acceptable acids such as hydrochloric, methanesulfonic, sulfuric, acetic, maleic, fumaric, phosphoric and the like. The salts are prepared by contacting the free base form with a sufficient amount of the desired acid to produce a salt in the conventional manner. The free base form may be regenerated by treating the salt forms with a base. For example, dilute aqueous base solutions may be utilized. Dilute aqueous sodium hydroxide, potassium carbonate, ammonia, and sodium bicarbonate solutions are suitable for this purpose. The free base form differs from the respective salt forms somewhat in certain physical properties such as solubility in polar solvents, but the salts are otherwise equivalent to the respective free base form for purposes of the invention.

The compounds of the invention and their corresponding salts can exist in unsolvated as well as solvated forms, including hydrated forms. In general, the solvated forms, with pharmaceutically acceptable solvents such as water, ethanol and the like are equivalent to the unsolvated forms for purposes of the invention.

The compounds of the invention can be prepared by decarbalkoxylation of a compound of the formula II:

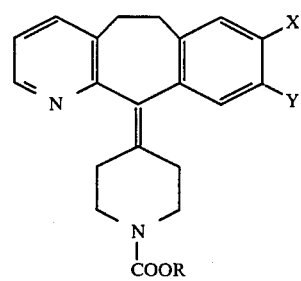

wherein R is an alkyl group (preferably ethyl) and X and Y are as defined above. The compounds of formula II can be prepared by procedures described in U.S. Pat. No. 4,282,233 from the corresponding N-alkyl (preferably N-methyl) compounds of formula III

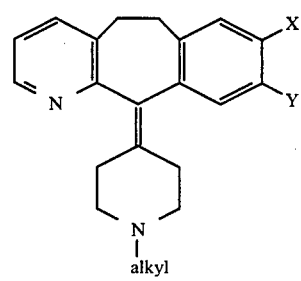

by employing appropriate starting materials having the desired X and Y substituents.

Alternatively, the compounds of the invention can be prepared by dealkylation of compounds of formula III, e.g., by reaction with cyanogen bromide and subsequent hydrolysis of the N-cyano product with, for example, aqueous acid solution to provide the compounds of formula I.

The compounds of formula III can be produced by the procedures described in U.S. Pat. No. 3,326,924 by employing the appropriately X and Y substituted starting materials. For example, 2-cyano-3-picoline of formula IV can be reacted with an appropriate benzaldehyde of formula V in the presence of a strong base such as potassium butoxide to give an ortho-phenethenyl pyridine carboxamide of formula VI

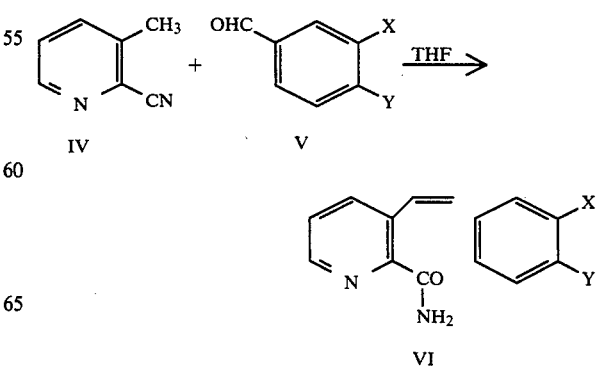

which is then hydrogenated, e.g., by employing a noble metal on carbon catalyst such as palladium or platinum on carbon, to the corresponding ortho-phenethyl pyridine carboxamide of formula VII

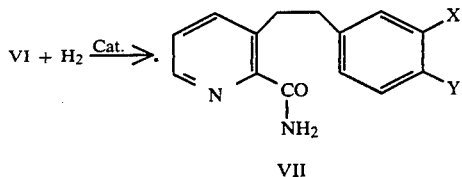

VII which in turn is hydrolyzed, e.g, with base such KOH, to the otho-phenethyl pyridine carboxylic acid of formula VIII

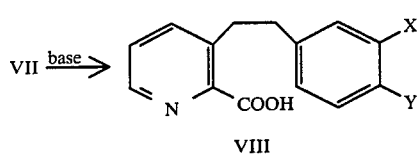

VIII

The compound of formula VIII can be cyclized, e.g., with oxalyl chloride and aluminum trichloride, to a compound of formula IX

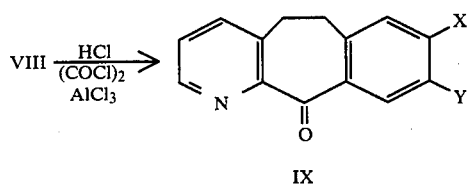

IX which is reacted with, for example, a Grignard reagent prepared from a 4-halo-N-alkyl-piperidine to produce the compound of formula X

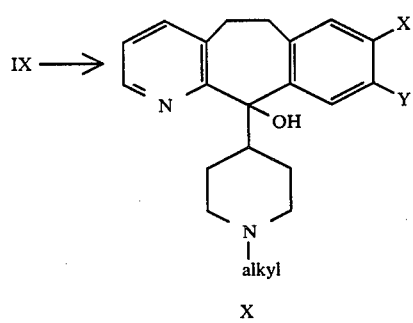

X which in turn is dehydrated, e.g., by acid such as polyphosphoric acid or sulfuric acid, to the compound of formula III:

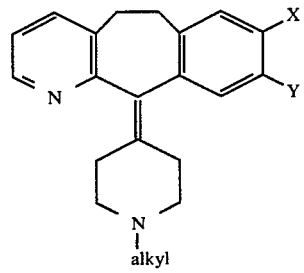

III

The compound of formula IX may also be reacted with Na in liquid $NH_3$ and a 4-halo-N-alkyl-piperidine to produce the compound of formula X.

In an alternative method 2-cyano-3-methylpyridine can be reacted in a Ritter reaction with a tertiary butyl compound in an acid such as concentrated sulfuric acid or concentrated sulfuric acid in glacial acetic acid to form a compound of formula XI

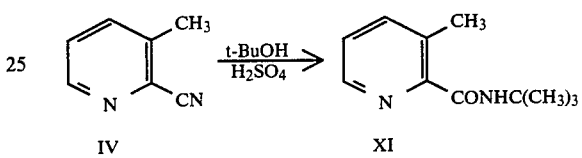

Suitable tertiary butyl compounds include, but are not limited to, t-butyl alcohol, t-butyl chloride, t-butyl bromide, t-butyl iodide, isobutylene or any other compound which under hydrolytic conditions forms t-butyl carboxamides with cyano compounds. The temperature of the reaction will vary depending on the reactants, but generally the reaction is conducted in the range of from about 50° C. to about 100° C. with t-butyl alcohol. The reaction may be performed with inert solvents but is usually run neat.

The product of the Ritter reaction (formula XI) can be reacted with an appropriate 3 and/or 4-halo or trifluoromethyl-substituted benzyl halide, in the presence of a base to form the compound of formula XII

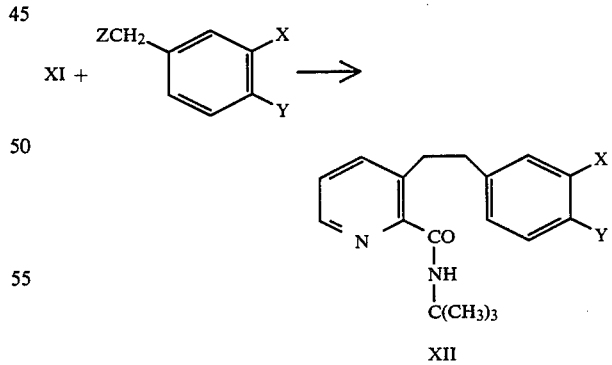

XII wherein Z is chloro, bromo or iodo. Examples of appropriate benzyl halides include, but are not limited to, 3-chloro-benzyl chloride, 3-fluoro-benzyl bromide, 3,4-dichloro-benzyl chloride, 4-fluoro-benzyl chloride, 3-trifluoromethyl-benzyl chloride, 3-bromobenzyl chloride, etc. Any suitable base can be employed e.g., an alkyl lithium compound such as n-butyl lithium in tetrahydrofuran (THF). Preferably the base has a $pK_a$ of greater than 20 and more preferably greater than 30.

This reaction can be conducted at any suitable temperature, e.g., temperatures of from about −78° C. to about 30° C., preferably from about −40° C. to about −30° C. The reaction can be performed in any suitable inert solvent such as THF, diethyl ether, etc.

The tertiary-butyl amide of formula XII can be converted to the cyano compound of formula XIII

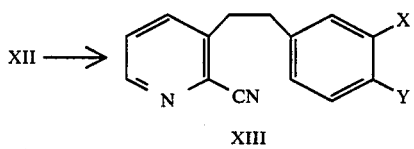

by the use of a suitable dehydrating agent such as POCl₃, SOCl₂, P₂O₅, toluene sulfonyl chloride in pyridine, oxalyl chloride in pyridine, etc. This reaction can be performed in the absence of or with a co-solvent such as xylene. The dehydrating agent such as POCl₃ is employed in equivalent amounts or greater and preferably in amounts of from about 2 to about 15 equivalents. Any suitable temperature and time can be employed for performing the reaction, but generally heat is added to speed up the reaction. Preferably, the reaction is performed at or near reflux.

The cyano compound of formula XIII can then be reacted with a Grignard reagent prepared from the appropriate 1-alkyl-4-halopiperidine. This reaction is generally performed in an inert solvent such as an ether, toluene or tetrahydrofuran. This reaction is performed under the general conditions for a Grignard reaction, e.g., at temperatures of from about 0° C. to about 75° C. The resulting compound of formula XIV

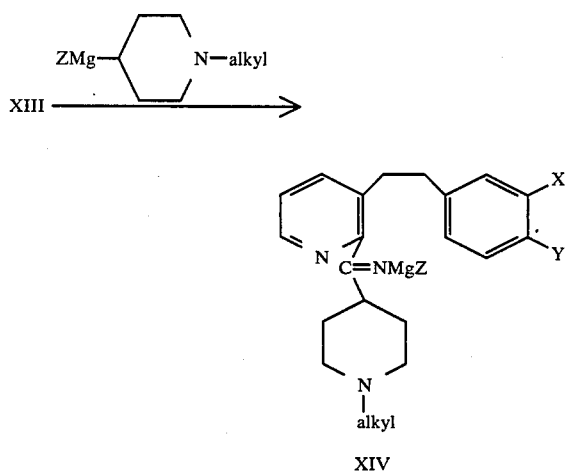

(wherein Z is again chloro, bromo or iodo) is hydrolyzed, e.g., by reaction with aqueous acid such as aqueous HCl to prepare the corresponding ketone of formula XV

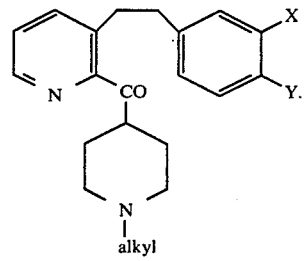

The compound of formula XV can be ring-closed to form the desired cycloheptene ring system by treating the compound XV with a super acid having a Hammett acidity function of less than about minus 12, e.g., minus 13, minus 14, etc., to produce a compound of formula III. This measure of acidity is defined in Hammett, Louis P., and Deyup, Alden J., *Journal of the American Chemical Society*, Vol. 54, 1932, p. 2721. Suitable super acids for this purpose include, for example, HF/BF₃, CF₃SO₃H, CH₃SO₃H/BF₃, etc. The reaction can be performed in the absence of or with an inert co-solvent such as CH₂Cl₂. The temperature and time of the reaction vary with the acid employed. For example, with HF/BF₃ as the super acid system the temperature may be controlled so as to minimize side reactions, such as HF addition to the double bond of the rings. For this purpose, the temperature is generally in the range of from about +5° C. to −50° C., preferably from about −30° C. to −35° C. With CF₃SO₃H as the super acid system, the reaction may be run at elevated temperatures, e.g., from about 25° C. to about 150° C. and at lower temperatures but the reaction then takes longer to complete.

Generally the super acid is employed in excess, preferably in amounts of from about 1.5 to about 30 equivalents. For example, with HF/BF₃ as the super acid system the molar ratio of HF to the compound of formula XV in the reaction mixture is preferably from about 30 to about 1.5, more preferably 2.5 to 1.5. In such system, the molar ratio of BF₃ to the compound of formula XV in the reaction mixture is preferably from about 15 to about 0.75, more preferably from about 1 to about 0.75.

As another alternative, a compound of formula XII above can be cyclized by use of super acid such as CF₃SO₃H or HF/BF₃ to produce a compound of formula IX.

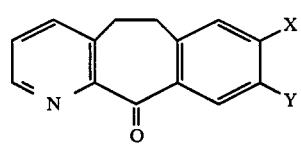

The compounds of formula IX may then be converted to the desired compounds of the invention as described above.

For preparing pharmaceutical compositions from the compounds described by this invention, inert, pharmaceutically acceptable carriers can be either solid or liquid. Solid form preparations include powders, tablets, dispersible granules, capsules, cachets and suppositories. A solid carrier can be one or more substances which may also act as diluents, flavoring agents, solubilizers, lubricants, suspending agents, binders or tablet disintegrating agents; it can also be an encapsulating material. In powders, the carrier is a finely divided solid which is in admixture with the finely divided active compound. In the tablet the active compound is mixed with carrier having the necessary binding properties in suitable proportions and compacted in the shape and size desired. The powders and tablets preferably contain from about 5 to about 20 percent of the active ingredient. Suitable solid carriers are magnesium carbonate, magnesium stearate, talc, sugar, lactose, pectin, dextrin, starch, gelatin, tragacanth, methylcellulose, sodium carboxymethyl-cellulose, a low melting wax, cocoa butter and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and therey solidify.

Liquid form preparations include solutions, suspensions and emulsions. As an example may be mentioned water or water-propylene glycol solutions for parenteral injection. Liquid preparations can also be formulated in solution in aqueous polyethylene glycol solution. Aqueous solutions suitable for oral use can be prepared by adding the active component in water and adding suitable colorants, flavors, stabilizing, sweetening, solubilizing and thickening agents as desired. Aqueous suspensions suitable for oral use can be made by dispersing the finely divided active component in water with viscous material, i.e., natural or synthetic gums, resins, methylcellulose, sodium carboxymethylcellulose and other well-known suspending agents.

Also included are solid form preparations which are intended to be converted, shortly before use, to liquid form preparations for either oral or parenteral administration. Such liquid forms include solutions, suspensions and emulsions. These particular solid form preparations are most conveniently provided in unit dose form and as such are used to provide a single liquid dosage unit. Alternately, sufficient solid may be provided so that after conversion to liquid form, multiple individual liquid doses may be obtained by measuring predetermined volumes of the liquid form preparation as with a syringe, teaspoon or other volumetric container. When multiple liquid doses are so prepared, it is preferred to maintain the unused portion of said liquid doses at low temperature (i.e., under refrigeration) in order to retard possible decomposition. The solid form preparations intended to be converted to liquid form may contain, in addition to the active material, flavorants, colorants, stabilizers, buffers, artificial and natural sweeteners, dispersants, thickeners, solubilizing agents and the like. The solvent utilized for preparing the liquid form preparation may be water, isotonic water, ethanol, glycerine, propylene glycol and the like as well as mixtures thereof. Naturally, the solvent utilized will be chosen with regard to the route of administration, for example, liquid preparations containing large amounts of ethanol are not suitable for parenteral use.

The composition of the invention may also be deliverable transdermally, e.g., with a transdermally acceptable carrier. The transdermal compositions can take the form of creams, lotions and/or emulsions, can be included in an appropriate adhesive for application to the skin or can be included in a transdermal patch of the matrix or reservoir type as are conventional in the art for this purpose.

Preferably, the transdermally acceptable composition is utilized to prepare a "reservoir type" or "matrix type" patch which is applied to the skin and worn for a specific period of time to permit the penetration of a desired amount of a compound of formula I through the skin. Most preferably, the patch of the invention will be worn for a period of about 24 hours and provide a total daily dosage of about 1 mg to about 40 mg, preferably from about 5 mg to about 10 mg, of a compound of the invention. The patch may then be replaced if necessary with a fresh patch, thereby providing a constant blood level of a compound of formula I to the patient in need thereof.

The utilization of this new transdermal dosage form and its prescribed regimen will provide the advantages described above. Other frequencies of dosage application are anticipated, for example, a once every 3 day frequency or a once every 7 day frequency. Although a once a day dosage regimen may be preferred, it is not intended that the invention be limited to any particular regimen.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules and powders in vials or ampoules. The unit dosage form can also be a capsule, cachet or tablet itself or it can be the appropriate number of any of these packaged form.

The quantity of active compound in a unit dose of preparation may be varied or adjusted from 1 mg to 1000 mg according to the particular application. The compositions can, if desired, also contain other therapeutic agents, such as decongestants.

The dosages may be varied depending upon the requirements of the patient and the severity of the condition being treated. Determination of the proper dosage for a particular situation is within the skill of the art. For convenience, the total daily dosage may be divided and administered in portions during the day if desired.

The compounds of the invention possess antihistaminic properties. The antihistaminic properties of these compounds may be demonstrated by use of standard pharmacological testing procedures. For example, the ability of the compounds to reduce histamine-induced paw edema in mice may be measured by use of the following method.

Male $CF_1$ mice, 25–30 g, are housed under conditions of controlled temperature and humidity with a 12 hour dark/light cycle. Food and water are allowed ad libitum. The mice are randomly assigned to the treatment groups. One hour after treatment with a compound of the invention or vehicle, the mice are lightly anesthetized with ether. The left hind paw of each mouse serves as a control and is injected with 25 $\mu$l of isotonic saline. The right hind paw serves as the experimental paw and is injected with 25 μl of isotonic saline containing 13 μg histamine dihydrochloride. Thirty minutes later the mice are killed by cervical dislocation and both hind paws of each mouse are removed by cutting at the tarsal joint. The weight of each paw is recorded and the difference in weight between the compound-treated and the placebo-treated groups is evaluated using Student's "t" test. The $ED_{50}$ values (the dose causing 50% inhibition of histamine-induced edema) and 95% confidence limits are determind by the Linear Least Square Dose-Response method [Brownlee, K. A., "Statistical Theory And Methodology In Science and Engineering", 2nd Ed., J. Wiley and Sons, New York, 1965, pp. 346-349]. The compounds of 8-chloro-6,11-dihydro-11-(4-piperidylidene)-5H-benzo[5,6]cyclohepta[1,2-b]pyridine (Compound A) and 8-fluoro-6,11-dihydro-11-(4-piperidylidene)-5H-benzo[5,6]cyclohepta[1,2-b]pyridine (Compound B) were tested by this procedure with the results shown in Table 1 below:

TABLE 1

| Treatment | Oral Dose mg/kg | No. of Animals | Increased Paw Weight (mg) Mean | % Inhibition | Oral $ED_{50}$ (mg/kg) |
|---|---|---|---|---|---|
| Placebo | — | 7 | 22.3 | — | — |
| Compound A | 0.03 | 8 | 19.9 | 11 | |
|  | 0.1 | 7 | 13.0 | 42 | |
|  | 0.3 | 8 | 6.1 | 73 | 0.15 |
|  | 1.0 | 8 | 2.5 | 89 | |
| Compound B |  |  |  |  | <3 |

Compounds A and B were also tested for antihistaminic activity by the procedures set forth in paragraph A below and for CNS activity by the procedures set forth in paragraphs B, C, and D below.

A. Prevention of histamine-induced lethality in guinea pigs. Compounds A and B were evaluated for their ability to protect female albino guinea pigs (250-350 g) against death induced by the intravenous injection of histamine dihydrochloride at 1.1 mg/kg, which is approximately twice the $LD_{99}$. Doses of the antagonists were administered orally to separate groups of fasted animals 1 hour prior to the challenge with histamine and protection from death recorded for 30 minutes after histamine. $ED_{50}$ values were determined for each drug by prohibit analysis.

B. Antagonism of Physostigmine Lethality. The physostigmine-induced lethality test used was a modification of the technique reported by COLLIER et al., Br. J. Pharmac., 32, 295-310 (1968). Physostigmine salicylate (b 1.0 mg/kg s.c.) produces 100% lethality when administered to mice grouped 10 per plastic cage (11×26×13 cm). Test agents were administered orally 30 minutes prior to physostigmine. The number of survivors were counted 20 minutes after physostigmine administration.

C. Antagonism of Acetic Acid Writhing. The acetic acid writhing test used was essentially that described by HENDERSHOT and FORSAITH, J. Pharmac. Exp. Ther., 125, 237-240 (1959), except that acetic acid rather than phenylquinone was used to elicit writhing. Mice were injected with 0.6% aqueous acetic acid at 10 mg/kg i.p. 15 minutes after oral administration of the test drug. The number of writhes for each animal was counted during a 10 minute period starting 3 minutes after acetic acid treatment. A writhe was defined as a sequence of arching of the back, pelvic rotation and hind limb extension.

D. Antagonism of Electro-Convulsive Shock (ECS). For the ECS test, a modification of the method of TOMAN et al., J. Neurophysiol., 9, 231-239 (1946), was used. One hour after oral administration of the test drug or vehicle, mice were administered a 13 mA, 60 cycle a.c. electroconvulsant shock (ECS) for 0.2 seconds via corneal electrodes. This shock intensity produces tonic convulsions, defined as extension of the hind limbs, in at least 95% of vehicle-treated mice.

Of the above test procedures for measuring CNS activity of antihistamines, the physostigmine-induced lethality test is believed to be a major index of non-sedating characteristics, since it reflects mainly central anticholinergic potency which is believed to contribute to sedative activity.

The results from the above test procedures are set forth in Table 2 below:

TABLE 2

| | Antihistaminic Activity | CNS Activity | | |
|---|---|---|---|---|
| | A. G. pig. | B. Physostigmine | C. Acetic | D. ECS |
| Compound | p.o. $ED_{50}$ (mg/kg) | lethality $ED_{50}$ (mg/kg) | writhing $ED_{50}$ (mg/kg) | test $ED_{50}$ (mg/kg) |
| A | 0.15 | 320 | 147 | 160 |
| B | .09 | 320 | 320 | 320 |

The above results demonstrate that the compounds of the invention are a potent antihistamines having low CNS activity indicative of non-sedation. Specifically, Compounds A and B are relatively inactive in all of the CNS test procedures, and in particular, they provide an $ED_{50}$ in the physostigmine-induced lethality test of greater than 320.

Compound A was also tested to assess its sedative effects in another procedure:

Acute behavioral, neurologic and autonomic effects of Compound A were evaluated in mice by a modification of the method of Irwin [Irwin S., Drug Screening And Evaluation Of New Drugs In Animals, in Animal And Clinical Pharmacologic Techniques in Drug Evaluation, Nodine JM and Siegler PE (Eds)., Year Book Medical Publishers Inc., Chicago 1964, pp 36-54]. After oral administration of vehicle or drug, mice (CFI males, 20-24 g) were observed and manipulated to evaluate behavorial, neurologic and autonomic changes. A semi-quantitative scoring scale was used where signs normally present (e.g., spontaneous activity, alertness, pupil size) were assigned a "normal" score of 0 and scores of +1, +2 and +3 indicated slight, moderate and marked increases and scores of −1, −2 and −3 indicated slight, moderate and marked decreases from "normality". When a sign occurred that is not normally present (e.g., convulsions, tremors), its magnitude was graded on a 1-3 scale. Each treatment group consisted of 6 animals and evaluations were conducted 1 hour after dosing. Additional observations for lethality were made for up to 24 hours after dosing. Incidence is defined as the observation occurring in an animal with a score of 2 or greater according to the scoring method defined above.

Effects of Compound A on behavior, neurologic function and automatic function in mice

| Measurement | MED, mg/kg po[a] |
| --- | --- |
| Lethality | 300 |
| Reactivity | 300 |
| Decreased motor activity | 300 |
| Decreased muscle tone | 300 |
| Tremors/convulsions | 300 |
| Ataxia | 300 |
| Mydriasis | 300 |
| Ptosis | 300 |

[a]Minimal effective dose, defined as the lowest dose that produced a score of 2 or greater according to Irwin (supra) in at least 3 of 6 animals tested at each dose.

From the above test results, it may be concluded that the compounds of the invention would be essentially non-sedating at a clinically useful antihistamic dosage. Compound B (i.e., the 8-fluoro compound) is particularly preferred because it has also shown very low toxicity.

The amount and frequency of administration of the compounds of the invention and the pharmaceutically acceptable salts thereof will be regulated according to the judgment of the attending clinician considering such factors as age, condition and size of the patient as well as severity of the symptom being treated. A typical recommended dosage regimen is oral administration of from 5 to 100 mg/day, preferably 10 to 20 mg/day, in two to four divided doses to achieve relief of the symptoms.

The following examples are intended to illustrate, but not to limit, the present invention.

EXAMPLE I

A.

N-(1,1-Dimethylethyl)-3-methyl-2-pyridine carboxamide 2-cyano-3-methyl pyridine (400 g) is suspended in t-BuOH (800 mL) and the mixture heated to 70° C. Concentrated sulphuric acid (400 mL) is added dropwise over 45 minutes. The reaction is complete after a further 30 minutes at 75° C. The mixture is then diluted with water (400 mL), charged with toluene (600 mL) and brought to pH 10 with concentrated aqueous ammonia. The temperature is kept at 50°–55° C. during the work up. The toluene phase is separated, the aqueous layer reextracted and the combined toluene phases are washed with water. Removal of the toluene yields an oil, N-(1,1-dimethylethyl)-3-methyl-2-pyridine carboxamide, from which solid product may crystallize. Product yield of 97% is determined by internal standard assay on gas chromatograph.

B.

3-[2-(3-Fluorophenyl)ethyl]-N-(1,1-dimethylethyl)-2-pyridine carboxamide

Tetrahydrofuran (125 mL) and N-(1,1-dimethylethyl)-3-methyl-2-pyridine carboxamide (1 equivalent) are charged and cooled to −40° C. under nitrogen. Two equivalents of n-butyllithium are then added over 40 minutes. When half the n-butyllithium is added the mixture turns purple. Sodium bromide (1.3 g) is added and then 3-fluoro-benzyl bromide (1.05 equivalents) is added dropwise (1:1 solution in tetrahydrofuran) over 40–50 minutes while the temperature is maintained at −40° C. After 30 minutes at −40° C., the mixture is diluted with water (250 mL) and the organic phase separated. This phase is dried over sodium sulphate and the solvent removed yielding an oil from which solid product, 3-[2-(3-fluorophenyl)ethyl]-N-(1,1-dimethylethyl)-2-pyridine carboxamide, may crystallize.

C.

3-[2-(3-Fluorophenyl)ethyl]-2-pyridine-carbonitrile

A solution of 3-[2-(3-fluorophenyl)ethyl]-N-(1,1-dimethylethyl)-2-pyridine carboxamide (36.4 g, 0.121 mole) in 123 mL (202.3 g, 1.32 mole) of phosphorous oxychloride is heated at 110° C. for 3.5 hours and stirred at ambient temperature an additional 15 hours. The reaction is quenched with ice and water and the pH of the solution is brought to 8 by the addition of a saturated aqueous solution of potassium carbonate. The product is extracted into ethyl acetate and the solution is concentrated to a residue. Following purification by silica gel chromatography and trituration with pentane, 16.2 g (0.072 mole) of product is obtained in 60% yield.

D.

(1-Methyl-4-piperidinyl)[3-[2-(3-fluorophenyl)ethyl]-2-pyridinyl]methanone

To a solution of 3-[2-(3-fluorophenyl)ethyl]-2-pyridine carbonitrile (28.0 g, 0.123 mole) in 150 mL of dry THF is added 92 mL (1.48 moles/liter, 0.136 mole) of N-methylpiperidyl magnesium chloride over 10 minutes maintaining the temperature of 45°–50° C. The reaction is maintained at 40° C. to 50° C. for another 10 minutes and at ambient temperature for 45 minutes. The reaction is quenched to below pH 2 and aqueous hydrochloric acid and the resulting solution is stirred at 25° C. for 1 hour. The pH of the solution is adjusted to about 8, the product is extracted with ethylacetate, and the solution is concentrated to a residue. Following purification by silica gel chromatography, 38.3 g of product is obtained as a brown oil.

E.

8-Fluoro-11-(1-methyl-4-piperidylidene)-6,11-dihydro-5H-benzo[5,6]cyclohepta[1,2-b]pyridine A solution of (1-methyl-4-piperidinyl)[3-[2-(3-fluorophenyl)ethyl]-2-piperidinyl]methanone (15.0 g, 0.046 mole) in 74 mL (125.5 g, 0.837 mole) of trifluoromethanesulfonic acid is stirred at ambient temperature for 18 hours. The reaction is quenched with ice-water and the solution made basic with potassium hydroxide. The product is extracted into ethyl acetate. The ethyl acetate solution is filtered to remove insolubles and the filtrate is concentrated to a residue. Following purification by silica gel chromatography, 5.4 g (0.0175 mole) of product is obtained in 38% yield.

F.

8-Fluoro-11(1-ethoxycarbonyl-4-piperidylidene)-6,11-dihydro-5H-benzo[5,6]cyclohepta[1,2-b]pyridine To a stirred solution of 8-fluoro-11-(1-methyl-4-piperidylidene)-6,11-dihydro-5H-benzo[5,6]cyclohepta[1,2-b]pyridine (10.5 g, 34 mmol) and triethylamine (5.2 g, 52 mmol) in dry toluene (120 mL) at 80° C. under an argon atmosphere, was added ethylchloroformate (18.5 g, 170 mmol) via a syringe. The reaction mixture was allowed to stir at this temperature for 30 minutes and at room temperature for one hour. The reaction mixture was then filtered and solvent was removed. The residue was triturated with pentane to give 10.1 grams (yield=81%) of the title compound, m.p.=116°-118° C.

G.

8-Fluoro-11-(4-piperidylidene)-6,11-dihydro-5H-benzo[5,6]cyclohepta[1,2-b]pyridine 8-Fluoro-11-(1-ethoxycarbonyl-4-piperidylidene)-6,11-dihydro-5H-benzo[5,6]cyclohepta[1,2-b]pyridine (3.6 g, 9.8 mmol.) was refluxed with KOH (4.5 g) in 50 mL of ethanol/water (1:1) for 66 hours under an argon atmosphere. The reaction mixture was poured into a brine solution and extracted twice with ethyl acetate. The extracts were combined and then dried over $Na_2SO_4$ and filtered. Solvent was removed to give 2.76 grams (yield=95%) of the title compound, m.p.=133.5°-134.5° C.

EXAMPLE II

A.

3-[2-(3-Fluorophenyl)ethenyl]-picolinamide

A solution of 2-cyano-3-picoline (142 g, 1.2 mole) and 3-fluorobenzaldehyde (164 g, 1.32 mole) in 750 mL of dry tetrahydrofuran (THF) is prepared. This solution is added dropwise to a solution of 162.0 grams of potassium t-butoxide (1.44 mole) dissolved in 750 mL of dry THF at $-15°$ C. to $-20°$ C.

The addition requires ½ hour, and the temperature is maintained below $-15°$ C. The mixture is stirred at $-15°$ to $-20°$ C. for 1 hour, then at 0° to 5° C. for 2 hours.

Saturated $NH_4Cl$ solution (400 mL) is added to the mixtured followed by 250 mL of $H_2O$. The mixture is stirred for ½ hour, and the aqueous layer is separated and extracted with 300 mL of $CH_2Cl_2$, which is combined with the THF layer. The organic solution is washed with 400 mL of saturated $NH_4Cl$ solution, dried over $Na_2SO_4$, treated with charcol and filtered through diatomaceous earth.

The solvent is removed on a rotary evaporator, and the oily residue is dissolved in 350 mL of boiling toluene. The mixture is filtered hot to remove impurities and cooled overnight at 0° to 5° C. The off-white solid that precipitates is filtered, washed twice with 100 mL of cold toluene, and dried at 60° C. for 6 hours, yielding 122.1 grams (42.1%) of the title compound, m.p.=153°-155° C.

B.

3-[2-(3-Fluorophenyl)ethyl]-picolinamide

A solution is prepared by dissolving 121 grams of 3-[2-(3-fluorophenyl)ethenyl]-picolinamide (0.5 mole) in 500 mL of acetic acid. To the solution is added 8.0 grams of 5% Pd/C and the mixture is placed on a Parr hydrogenator overnight. A theoretical amount of $H_2$ is absorbed, and mixture is filtered through diatomaceous earth and poured into 4 liters of $H_2O$. The off-white suspension is stirred for 2 hours and cooled at 0° to 5° C. for 20 hours.

The solid product 3-[2-(3-fluorophenyl)ethyl]-picolinamide is filtered and washed three times with 100 mL of $H_2O$ and dried at 60° C. for 20 hours, yielding 108 grams (yield=88.6%) of the title compound, m.p.=102°-104° C.

C.

3-[2-(3-Fluorophenyl)ethyl]-picolinic acid

A suspension of 73.2 grams of 3-[2-(3-fluorophenyl)ethyl]-picolinamide (0.3 mole) in 500 mL of ethanol and 125 grams of 45% KOH (1.0 mole) is prepared. $H_2O$ (200 mL) is added, and the mixture is refluxed for 20 hours. TLC shows complete conversion to the acid.

The alcohol is removed by distillation until the vapor temperature reaches 100° C. The suspension is cooled to room temperature, 100 mL of $H_2O$ is added and the solution is brought to a pH of 4-4.5 with 12N HCl (110 mL). The suspension is stirred for 1 hour and cooled overnight. The solid is filtered, washed three times with 100 mL of $H_2O$ and dried at 65° C. for 24 hours, yielding 69.6 grams (yield=94.8%) of the title compound, m.p.=118°-122° C.

D.

8-Fluoro-6,11-dihydro-5H-benzo-[5,6]-cyclohepta[1,2-b]pyridin-11-one

A solution of 61.3 grams of 3-[2-(3-fluorophenyl)ethyl]-picolinic acid (0.25 mole) in 900 mL of tetrachloroethane is prepared. Anhydrous HCl gas is passed through the solution at room temperature for 1½ hours. Oxalylchloride (48.3 grams, 0.38 mole) is carefully added, and stirred for 24-26 hours at room temperature (slight heating at 35°-40° C. for 4 hours is needed to obtain a dark solution). The solution is cooled to 0°-5° C., and 67 grams of $AlCl_3$ (0.5 mole) are slowly added over ½ hour. The mixture is stirred at 0° to 5° C. for 18 hours. An additional 17 grams of $AlCl_3$ (0.125 mole) is added, and mixture is stirred for 2 hours.

Then 500 mL of 3.7% HCl is added, and the mixture is stirred for ¼ hour and filtered through diatomaceous earth. The top aqueous layer is separated, and the organic layer is washed twice with 500 mL of 3.7N HCl. The combined aqueous layer is washed twice with 500 mL of ether.

Benzene (1 liter) is added. The mixture is cooled to 5°-10° C. and brought to pH>9 with slow addition of 390 grams of 50% NaOH. The mixture is stirred for ½ hour and filtered through diatomaceous earth. The aqueous layer is separated and washed twice with 300 mL of benzene, which are combined with the first benzene layer.

The combined organic layers are washed with 250 mL of 5% $NaHCO_3$ and 250 mL of saturated NaCl solution. The organic layer is dried over $Na_2SO_4$, and solvent is removed leaving 49.6 grams of a yellow solid. The solid is dissolved in 100 mL of butyl acetate (hot) and cooled for 24-48 hours at 0° to 5° C. The solid is filtered, washed twice with 30 mL of cold ethyl acetate, and dried at 60° C. for 20 hours, yielding 38.8 grams (yield=68.5%) of the title compound, m.p.=116°-119° C.

E.

1-Methyl-4-[8-fluoro-6,11-dihydro-5H-benzo[5,6]cyclohepta[1,2-b]pyridin-11-yl]piperidin-11-OL A suspension is prepared by mixing 22.7 grams of 11-oxo-8-fluoro-6,11-dihydro-5H-benzo[5,6]cyclohepta[1,2-b]pyridine (0.1 mole) with 500 mL of liquid $NH_3$, and 5.1 grams of Na(0.22 mole) are added. The resulting blue mixture is stirred for ¾ hour. A solution containing 15.9 grams of 4-chloro-N-methyl-piperidine (0.12 mole)

in 400 mL of dry THF is slowly added over ½ hour and stirred for 2 hours at −25° C.

NH$_4$Cl (17.5 grams, 0.33 mole) is added, and the mixture is stirred for ½ hour until the mixture warms to 0° C. Saturated NH$_4$Cl solution (200 mL) is added, followed by 50 mL of H$_2$O, and mixture is stirred for ¼ hour.

The aqueous layer is separated and extracted with 200 mL of CH$_2$Cl$_2$, which is combined with the THF layer. The combined organic layer is washed with 250 mL of saturated NH$_4$Cl solution, and dried over Na$_2$SO$_4$. The solvent is removed, leaving 34.7 grams of an oil, which crystallizes upon cooling.

The solid material is dissolved in 65 mL of hot n-butyl acetate and cooled overnight. The solid obtained is filtered, washed twice with 15 mL of cold ethyl acetate, and then dried at 75° C. for 6 hours, yielding 15.8 grams of the title compound, m.p.=123.5°–125° C.

The solvent is removed from the filtrate, leaving 11.0 grams of a yellow solid, which is dissolved in 20 mL boiling ethyl acetate, filtered hot, and cooled at 0°–5° C. for 4 hours. The solid obtained is filtered, washed twice with 5 mL of ethyl acetate, and dried at 60° C. for 5 hours, yielding 4.3 grams (total yield=61.7%).

F.

8-Fluoro-11-(1-methyl-4-piperidylidene)-6,11-dihydro-5H-benzo[5,6]cylohepta[1,2-b]pyridine A solution of 13.1 grams of 1-methyl-4-[8-fluoro-6,11-dihydro-11-hydroxy-5H-benzo-[5,6]cyclohepta[1,2-b]pyridin-11-yl]piperidine (0.04 mole) in 40 mL of 93% H$_2$SO$_4$ is prepared. The solution is stirred overnight at room temperature. CH$_2$Cl$_2$ (200 mL) is added, and with external cooling, the mixture is neutralized to pH>9 using 50% NaOH, while maintaining the temperature below 30° C. The aqueous layer is separated and re-extracted twice with 150 mL of CH$_2$Cl$_2$, which is combined with the first layer. The combined organic layer is washed with 150 mL of saturated NaHCO$_3$ solution and 150 mL of saturated NaCl solution, dried over Na$_2$SO$_4$, treated with charcoal and filtered through diatomaceous earth. The solvent is removed on a rotary evaporator leaving 12.9 grams of a yellow oil, which solidified upon standing.

The oil is dissolved in 70 mL of hot diisopropyl ether (6 parts) and poured into a hot solution of 9.5 grams of maleic acid (0.082 mole) dissolved in 60 mL of diisopropyl ether. The solution is cooled to 0°–5° C. with stirring and a yellow oil forms. The mixture is cooled overnight at 0°–5° C. with a yellow solid forming. The solid is filtered, washed twice with 20 mL of cold diisopropyl ether, and dried at 60° C. for 4 hours, yielding 18.2 grams.

This solid is dissolved in 2 parts boiling diisopropyl ether and filtered hot. The filtrate is cooled at 0°–5° C. with stirring for 1 hour with a heavy white precipitate forming. The suspension is cooled at 0°–5° C. for 6 hours. The solid formed is filtered, washed three times with 15 mL of cold diisopropyl ether and dried at 75°–80° C. for 48 hours, yielding 15.6 grams (yield=72.2%) of the title compound, m.p.=151°–152° C.

The product of step F above can then be employed in the process described in Example 1.F. and 1.G. to provide 8-fluoro-11-(1-ethoxycarbonyl-4-piperidylidene)-6,11-dihydro-5H-benzo[5,6]cyclohepta[1,2-b]pyridine and 8-fluoro-11-(4-piperidylidene)-6,11-dihydro-5H-benzo[5,6]cyclohepta[1,2-b]pyridine, respectively.

EXAMPLE III

8-Chloro-6,11-dihydro-11-(4-piperidylidene)-5H-benzo[5,6]cyclohepta[1,2-b]pyridine acetic acid salt To 12 grams of sodium hydroxide in 30 mL ethyl alcohol (70%) add 6 grams of 8-chloro-6,11-dihydro-11-(1-ethoxy-carbonyl-4-piperidylidene)-5H-benzo[5,6]cyclohepta[1,2-b]pyridine (prepared as described in U.S. Pat. No. 4,282,233) and reflux with stirring for 24 hours. After about the first 6–8 hours an additional 30 mL of 70% ethyl alcohol may be added.

Remove about 50% of the solvent by distillation in vacuo. Add a small amount of ice water and acidify with glacial acetic acid.

Extract with chloroform (6–8×), since the product precipitates from the acetic acid solution as a thick emulsion which cannot be filtered.

Concentrate the chloroform extracts to a small volume and precipitate the product with hexane. Crude m.p. 197°–200° C.

Recrystallize from benzene-hexane to obtain the product, m.p. 199°–200° C. Yield 4.0–4.5 grams.

EXAMPLE IV

B.

3-[2-(3-Chlorophenyl)ethyl]-N-(1,1-dimethylethyl)-2-pyridine carboxamide 31.5 g of N-(1,1-dimethylethyl)-3-methyl-2-pyridine carboxamide (e.g., as prepared in step A of Example I above) is dissolved in 600 mL of dry tetrahydrofuran and the resulting solution is cooled to −40° C. Two equivalents of n-butyllithium in hexane are added while the temperature is maintained at −40° C. The solution turned deep purple-red. 1.6 g of sodium bromide is added and the mixture is stirred. A solution of 26.5 g (0.174 mole) m-chlorobenzylchloride in 125 mL of tetrahydrofuran is added while the temperature is maintained at −40° C. The reaction mixture is stirred until the reaction is complete as determined by thin layer chromatography. Water is added to the reaction until the color is dissipated. The reaction mixture is extracted with ethyl acetate, washed with water, and concentrated to a residue. A yield of 92% for the product is shown by chromatography.

C.

3-[2-(3-Chlorophenyl)ethyl]-2-pyridine-carbonitrile

A solution of 3-[2-(3-chlorophenyl)ethyl]-N-(1,1-dimethylethyl)-2-pyridine carboxamide (175 g, 0.554 mole), in 525 mL (863 g, 5.63 mole) of phosphorous oxychloride is heated at reflux for 3 hours. Completion of the reaction is determined by thin layer chromatography. Excess phosphorous oxychloride is removed by distillation at reduced pressure and the residue is quenched into a mixture of water and isopropanol. The pH is brought to 5–7 by addition of 50% aqueous sodium hydroxide solution while maintaining the temperature below 30° C. The crystalline slurry of crude product is filtered and washed with water. Crude product is purified by slurrying the wet cake in hot isopropanol followed by cooling at 0°–5° C. The product is filtered, washed with hexane and dried at below 50° C. Yield: 118 g (HPLC purity 95.7%), m.p. 72°–73° C., 89.4% of theory.

D.

(1-Methyl-4-piperidinyl)[3-[2-(3-chlorophenyl)ethyl]-2-pyridinyl]methanone hydrochloride To a solution of product of Step C above (118 g, 0.487 mole) in 1.2 L of dry tetrahydrofuran is added 395 mL (2.48 mole/liter, 0.585 mole, 1.2 eg.) of N-methylpiperidyl magnesium chloride over about 15 minutes maintaining the temperature at 45° C.-50° C. by cooling with water as necessary. The reaction is maintained at 40° C. to 50° C. for about another 30 minutes. Completion of the reaction is determined by thin-layer chromatography. The reaction is quenched to pH below 2 with 2N hydrochloric acid and the resulting solution is stirred at about 25° C. for 1 hour. The bulk of the tetrahydrofuran is removed by distillation and the resulting solution is adjusted to pH 3.5 by the addition of aqueous sodium hydroxide. After cooling to 0° to 5° C., the crystalline hydrochloride salt product is filtered off, washed with ice cold water and dried to constant weight at 60° C. Yield: 168.2 g (HALC purity 94%), m.p. 183°-185° C., 89% of theory.

E.

8-Chloro-6,11-dihydro-11-(1-methyl-4-piperidylindene)5H-benzo[5,6]cyclohepta[1,2-b]pyridine To a solution of a product of Step D above (59 g, 0.15 mole) in 120 mL (120 g, 6.0 mole) of hydrofluoric acid at −35° C. is added boron trifluoridine (44.3 g, 0.66 mole) over 1 hour. Completeness of the reaction is determined by thin-layer chromatography. The reaction is quenched using ice, water and potassium hydroxide to a final pH of 10. The product is extracted into toluene and the toluene solution is washed with water and brine. The toluene solution is concentrated to a residue, which is dissolved in hot hexane. Insolubles are removed by filtration and the filtrate is concentrated to an off-white powder. Yield: 45.7 g (HPLC purity: 96%), 92% of theory.

Alternative Step E

8-Chloro-6,11-dihydro-11-(1-methyl-4-piperidylidene)-5H-benzo[5,6]cyclohepta[1,2-b]pyridine A solution of 177 g ( 0.49 mole) of a product of Step D above in 480 mL (814.1 g, 5.31 mole) of trifluoromethanesulfonic acid at 90°-95° C. for 18 hours under nitrogen. Completeness of the reaction is determined by thin-layer chromatography. The cooled reaction is quenched with ice-water and the pH is adjusted to 6 with barium carbonate. The product is extracted into methylene chloride, which is concentrated under reduced pressure to about 1 liter and washed with water. The product is extracted into 1N hydrochloric acid, which is treated with 30 g of Darco, and filtered through celite. The pH of the filtrate is adjusted to 10 with 50% aqueous sodium hydroxide and the product is extracted into methylene chloride, which is removed under reduced pressure. The residue is dissolved in hot hexane, which is filtered to remove insolubles. The filtrate is concentrated to a residual beige powder. Yield: 126 g (HPLC purity 80%), 65% of theory.

EXAMPLE V

8-Chloro-6,11-dihydro-11-(4-piperidylidene)-5H-benzo[5,6]cyclohepta[1,2-b]pyridine The acetic acid salt prepared as in Example II is dissolved in a minimum amount of water and the solution is made basic with a dilute aqueous solution of potassium carbonate. A pink colored oil separates.

Extract the organic material with chloroform, wash with water and remove the solvent. Triturate the residue with hexane. Recrystallize from a large volume of hexane after charcoal decolorization to obtain the product, m.p. 151°-152° C.

EXAMPLE VI

8-Chloro-6,11-dihydro-11-(4-piperidylidene)-5H-benzo[5,6]cyclohepta [1,2-b]pyridine

A.

8-chloro-6,11-dihydro-11-(1-cyano-4-piperidylidene)-5H-benzo[5,6]cyclohepta[1,2-b]pyridine.

Dissolve 16.2 grams (0.05 mole) of 8-chloro-6,11-dihydro-11-(1-methyl-4-piperidylidene)-5H-benzo[5,6-]cyclohepta[1,2-b]pyridine (prepared by the methods described in U.S. Pat. No. 3,326,924) in 300 mL of dry benzene. To this solution, add slowly under nitrogen a solution of cyanogen bromide (6.4 g) dissolved in 75 mL of benzene. Allow this mixture to stir at room temperature overnight (approximately 20 hours).

Filter the solution, and concentrate the filtrate in vacuo to a small volume and precipitate the product by the addition of petroleum ether or hexane until precipitation is complete. Filter and recrystallize from ethanol/water to yield the product 15 grams (89%), m.p. 140°-142° C.

Anal. Calcd. for $C_{20}H_{18}N_3Cl$: C,71.53; H,5.40; N,12.51. Found, C,71.73; H,5.43; N,12.27.

B.

8-Chloro-6,11-dihydro-11-(4-piperidylidene)-5H-benzo[5,6]cyclohepta[1,2-b]pyridine.

A solution of 14 grams of the N-cyano compound from part A in 60 mL of concentrated hydrochloric acid, 600 mL of glacial acetic acid and 400 mL of water is refluxed with stirring for 20 hours. The solvents are removed in vacuo and the residue dissolved in water and neutralized with ammonium hydroxide. The material is extracted several times with chloroform, the chloroform extracts washed with water and concentrated to dryness, and the residue triturated with petroleum ether or hexane to yield 11.5 grams (93%) m.p. 149°-151° C. After recrystallization from hexane, the product melts at 150°-151° C.

Anal. Calcd. for $C_{19}H_{19}N_2Cl$: C,73.42; H,6.16; N,9.01. Found: C,73.19; H,6.14; N,8.91.

EXAMPLE VII

A.

N-(1,1-dimethylethyl)-3-[2-(4-fluorophenyl)ethyl]-2-pyridine carboxamide

To a cooled (−40° C.) solution of N-(1,1-dimethylethyl)-3-methyl-2-pyridinecarboxamide (38.4 g, 0.2 mole) in dry THF (250 mL) is added n-butyl lithium (185 mL, 0.44 mole). Then sodium bromide (1.9 g, 18 mmol.) is added and is allowed to stir for 15 minutes. 4-Fluorobenzylchloride (31.8 g. 0.22 mole) was added and the reaction is allowed to stir for 2½ hours while warming up to −5° C. The reaction is then quenched with water and the product is extracted twice with ethyl acetate followed by washing twice with brine. The organic phase is dried over $Na_2SO_4$, filtered and solvent is removed to give desired compound (60.0 g) in 99% yield, m.p. 59°–61° C.

By a similar procedure, the corresponding 3-fluorophenyl, 3,4-dichlorophenyl, 3-bromophenyl, 4-chlorophenyl and 3,4-dibromophenyl analogs can be prepared by employing the appropriate substituted benzyl chloride.

B.

3-[2-(4-Fluorophenyl)ethyl]-2-pyridine-carbonitrile

The product of previous Step A (60.0 g, 0.2 mole) in $POCl_3$ (200 mL) is heated at 110° C. under an argon atmosphere for 3½ hours. The reaction mixture is poured onto ice and basified with 50% NaOH solution. It is then extracted three times with ethyl acetate, washed with water and brine, and dried over $Na_2SO_4$. Solvent is removed and the residue is passed through a coarse $SiO_2$ (60–200 mesh) column to give the desired product as a white solid (40 g) in 88% yield, m.p. 48°–49° C.

C.

9-Fluoro-5,6-dihydro-(1H)-benzo[5,6]cyclohepta[1,2-b]-pyridin-11-one

The product of Step B hereof (31.5 g, 139 mmol) is cyclized in polyphosphoric acid (1.24 kg) at 200° C. for 5½ hours. The hot reaction is poured into ice and then basified with 50% NaOH solution. The product is extracted three times with $CHCl_3$ and then washed with brine. The organic phase is dried ($Na_2SO_4$), filtered, and solvent is removed to give the desired product (20.4 g) in 64% yield, m.p. 78°–81° C. after recrystallization from diisopropyl ether.

D.

9-fluoro-6,11-dihydro-11-(1-methyl-4-piperidinyl)-5H-benzo[5,6]cyclohepta[1,2-b]pyridin-11-OL A solution of the product of previous Step C above (10.0 g, 44 mmol) in THF (100 mL) is added slowly to a cooled (−40° C.) solution of the Grignard reagent prepared from N-methyl-4-chloro-piperidine (57.9 mL, 88 mmol) in THF (70 mL). This is allowed to stir for about 1 hour while warming up to 0° C. The reaction is then quenched with $NH_4Cl$ solution and then extracted twice with ethyl acetate. The organic phase is washed with brine, dried over $Na_2SO_4$, filtered and solvent removed. The residue is flash chromatographed and eluted with 5% methanol in $CHCl_3$ to give the desired compound (10.1 g) in 70% yield as white granular crystals, m.p. 126°–127° C. after recrystallization from diisopropyl ether.

E.

9-Fluoro-11-[1-methyl-4-piperidylene]-6,11-dihydro-5H-benzo[5,6]cyclohepta[1,2-b]pyridine To an ice-bath-cooled acid (146 mL) of $H_2SO_4$ and $CF_3SO_3H$ (1:1) is added the product of previous Step D (7.3 g, 22.3 mmol). The reaction mixture is allowed to stir for ½ hour at ice bath temperature and then at room temperature for 1½ hour. The reaction mixture is poured onto ice and then basified with 50% NaOH solution. The product is extracted three times with ethyl acetate and washed with brine. The organic phase is desired ($Na_2SO_4$), filtered and solvent is removed to give a crude oil which is charcoaled and recrystallized from ethyl acetate and isopropyl ether to give the desired product (5.6 g) in 82% yield, m.p. 134.5°–135.5° C.

F.

9-fluoro-11-[1-ethoxycarbonyl-4-piperidylidene]-6,11-dihydro-5H-benzo[5,6]cyclohepta[1,2-b]pyridine To a stirred solution of the product of previous Step E (5.0 g, 16.2 mmol) and triethylamine (2.6 g, 26 mmol) in dry toluene (60 mL) at 80° C. under an argon atmosphere, is added ethylchloroformate (9.8 g, 90 mmol) via a syringe. The reaction is allowed to stir at this temperature for 30 minutes and at room temperature for an hour. The reaction is filtered and solvent is removed. The residue is passed through coarse $SiO_2$ (60–200 mesh), eluted with $CHCl_3$ to give the desired product (4.5 g) in 76% yield as a white solid, m.p. 112°–114° C. after trituration wih pentane.

G.

9-Fluoro-11-[4-piperidylidene]-6,11-dihydro-5H-benzo[5,6]cyclohepta[1,2-b]pyridine The product of previous Step F (3.83 g, 10.4 mmol) is refluxed with KOH (4.6 g) in 50 mL of ethanol/$H_2O$ (1:1) for 4 hours under an argon atmosphere. The reaction mixture is poured into a brine solution and extracted twice with ethyl acetate. It is then dried over $Na_2SO_4$ and filtered. Solvent is removed to give the named compound (2.86 g) in 90% yield, m.p. 138°–140° C.

EXAMPLE VIII

A.

3-[2-(3,4-Dichlorophenyl)ethyl]-2-pyridinecarbonitrile

A solution of 3-[2-(3,4-dichlorophenyl)ethyl]-N-(1,1-dimethylethyl)-2-pyridine carboxamide (37.8 g, 0.107 mole) in 120 mL (197.4 g, 1.29 mole) of phosphorous oxychloride is heated at 110° C. for 4.5 hours. Completion of the reaction is determined by thin-layer chromatography. The reaction is quenched with ice and $H_2O$ and the pH of the solution is brought to 8 by the addition of a saturated solution of potassium carbonate. The product is extracted into ethylacetate. The solution is concentrated to a solid residue which upon recrystallization from diethyl ether/ethyl acetate provides the desired product, (27.1 g, 0.098 mole), in 91.6% yield.

B.

(1-Methyl-4-piperidinyl)-[3-[2-(3,4-dichlorophenyl)ethyl]-2-piperidinyl]methanone To a solution of the product of previous Step A (21.2 g, 0.0765 mole) in 140 mL of dry tetrahydrofuran at reflux is added 50 mL (1.48 mole/liter, 0.074 mole) of N-methylpiperidyl magnesium chloride over about 10 minutes. The reaction is maintained at reflux for an additional 10 minutes. The reaction is quenched to pH below 2 with aqueous hydrochloric acid and the resulting solution is stirred at 25° C. for 1 hour. The pH of the solution is adjusted to about 8, the product is extracted with ethyl acetate and the solution is concentrated to a residue. Following purification by silica gel chromatography and crystallization from diisopropyl ether, the desired product (19.86 g, 0.0526 mole) is obtained in 69% yield.

C.

8,9-Dichloro-6,11-dihydro-11-(1-methyl-4-piperidylidene-5H-benzo[5,6]-cyclohepta[1,3-b[pyridine

A solution of the product of previous Step B (9.8 g, 0.0259 mole) in 100 mL (169.6 g, 1.13 mole) of trifluoromethanesulfonic acid is heated at 85° C. for 48 hours. The reaction is quenched with ice-water and the solution made basic with potassium hydroxide. The product is extracted into ethyl acetate and the solution is concentrated to a residue. Following purification by reverse phase HPLC and crystallization from acetone/pentane, the desired product (2.38 g, 0.0066 mole) is obtained in 25.5% yield.

D.

8,9-Dichloro-6,11-dihydro-11-(1-ethoxycarbonyl-4-piperidylidene)-5H-benzo[5,6]cyclohepta[1,2-b]pyridine

Ethyl chloroformate (1.9 mL, 2.16 g; 0.020 mole) in 10 mL of toluene is slowly added at 80° C. to a solution of the product of previous Step C (1.44 g, 0.004 mole) and triethylamine (1.5 mL, 1.09 g, 0.011 mole) in 50 mL of toluene. Folowing complete addition, the temperature is maintained at 80° C. for 2.5 hours. Insolubles in the reaction mixture are removed by filtration, and the filtrate is concentrated to a residue. Following silica gel chromotography and crystallization from pentane, the desired product (1.2 g, 0.0029 mole) is obtained in 72.5% yield.

E.

8,9-Dichloro-11-(4-piperidylidene)-6,11-dihydro-5H-benzo[5,6]cyclohepta[1,2-b]pyridine

A solution of the product of previous Step D (0.925 g, 0.0022 mole) and potassium hydroxide (1.5 g, 0.039 mole) in 7.5 mL of water and 8.5 mL of ethanol is heated at reflux for 27 hours. The reaction mixture is diluted with water and the product is extracted into ethyl acetate. The solution is concentrated to a residue and the named compound (0.685 g, 0.0020 mole) is obtained from crystallization with toluene. Yield 91%.

By employing the appropriately substituted benzyl chloride in Example I. B. above in place of 3-fluorobenzyl chloride, the following compounds of formula I or their pharmaceutically acceptable salts may also be prepared:

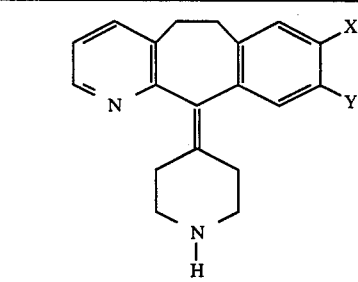

| Compound No. | X | Y |
| --- | --- | --- |
| 1 | H | Cl |
| 2 | H | Br |
| 3 | H | I |
| 4 | H | CF$_3$ |
| 5 | Br | H |

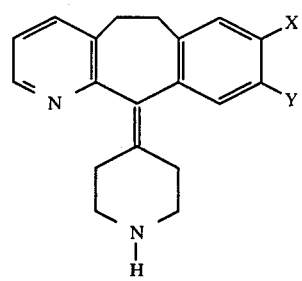

| Compound No. | X | Y |
| --- | --- | --- |
| 6 | I | H |
| 7 | CF$_3$ | H |
| 8 | F | F |
| 9 | Br | Br |
| 10 | Cl | F |
| 11 | Cl | Br |
| 12 | F | Cl |
| 13 | Br | Cl |
| 14 | F | Br |
| 15 | Br | F |

The following formulations exemplify some of the dosage forms of the compositions of this invention. In each, the term "active compound" designates a compound of the invention, e.g., Compound A or Compound B, or a pharmaceutically acceptable salt or solvate thereof.

PHARMACEUTICAL DOSAGE FORM EXAMPLES

EXAMPLE A

| | Tablets | | |
| --- | --- | --- | --- |
| No. | Ingredient | mg/tablet | mg/tablet |
| 1. | Active Compound | 100 | 500 |
| 2. | Lactose USP | 122 | 113 |
| 3. | Corn Starch, Food Grade, as a 10% paste in Purified Water | 30 | 40 |
| 4. | Corn Starch, Food Grade | 45 | 40 |
| 5. | Magnesium Stearate | 3 | 7 |
| | Total | 300 | 700 |

Method of Manufacture

Mix item nos. 1 and 2 in a suitable mixer for 10–15 minutes. Granulate the mixture with item no. 3. Mill the damp granules through a coarse screen (e.g., ¼") if needed. Dry the damp granules. Screen the dried granules if needed and mix with item no. 4 and mix for 10–15 minutes. Add item no. 5 and mix for 1–3 minutes. Compress the mixture to appropriate size and weight on a suitable tablet machine.

EXAMPLE B

| | Capsules | | |
| --- | --- | --- | --- |
| No. | Ingredient | mg/capsule | mg/capsule |
| 1. | Active Compound | 100 | 500 |
| 2. | Lactose USP | 106 | 123 |
| 3. | Corn Starch, Food Grade, | 40 | 70 |
| 4. | Magnesium Stearate NF | 4 | 7 |
| | Total | 250 | 700 |

Method of Manufacture

Mix item nos. 1, 2 and 3 in a suitable blender for 10–15 minutes. Add item no. 4 and mix for 1–3 minutes. Fill the mixture into suitable two-piece hard gelatin capsules on a suitable encapsulating machine.

EXAMPLE C

| Ingredient | Parenteral mg/vial | mg/vial |
|---|---|---|
| Active Compound Sterile Powder | 100 | 500 |

Add sterile water for injection or bacteriostatic water for injection, for reconstitution.

EXAMPLE D

| Ingredient | Injectable mg/vial |
|---|---|
| Active Compound | 100 |
| Methyl para-hydroxybenzoate | 1.8 |
| Propyl para-hydroxybenzoate | 0.2 |
| Sodium Bisulfite | 3.2 |
| Disodium Edetate | 0.1 |
| Sodium Sulfate | 2.6 |
| Water for Injection q.s. ad | 1.0 mL |

Method of Manufacture

1. Dissolve the para-hydroxybenzoates in a portion (85% of the final volume) of the water for injection at 65°–70° C.
2. Cool to 25°–35° C. Charge and dissolve the sodium bisulfite, disodium edetate and sodium sulfate.
3. Charge and dissolve active compound.
4. Bring the solution to final volume by adding water for injection.
5. Filter the solution through a 0.22 membrane and fill into appropriate containers.
6. Finally, sterilize the units by autoclaving.

The following examples illustrate formulations including a compound of formula I for transdermal application. Compound A refers to 8-chloro-6,11-dihydro-11-(4-piperidylidene)-5H-benzo[5,6]cyclohepta[1,2-b]pyridine, but again other compounds of formula I such as compound B above may be employed in its place.

EXAMPLE E

| Ointment | mg/g |
|---|---|
| Compound A | 200 |
| White Petrolatum | 800 |

EXAMPLE F

| Ointment | mg/g |
|---|---|
| Compound A | 200 |
| Propylene glycol | 200 |
| White Petrolatum | 600 |

EXAMPLE G

| Cream | mg/g |
|---|---|
| Compound A | 200 |
| Mineral Oil | 48 |
| White Petrolatum | 120 |
| Cetostearyl Alcohol | 57.6 |
| Polyethylene glycol 1000 monocetylether | 18.0 |
| Propylene glycol | 80 |
| Water | 476.4 |

EXAMPLE H

| Gel | mg/g |
|---|---|
| Compound A | 200 |
| Pluronic F-127 | 250 |
| Ethanol | 200 |
| Water | 350 |

EXAMPLE I

| Cream | mg/g |
|---|---|
| Compound A | 100.00 |
| Mineral Oil | 54.0 |
| White Petrolatum | 135.0 |
| Cetostearyl Alcohol | 65.0 |
| Ceteth 20 | 20.0 |
| Propylene Glycol | 100.0 |
| Water q.s. ad | 1.0 g |

The formulations of Examples E–I above can be packaged to produce a "reservoir type" transdermal patch with or without a rate-limiting patch membrane. The size of the patch and or the rate limiting membrane can be chosen to deliver the transdermal flux rates desired. Such a transdermal patch can consist of a polypropylene or polyester impervious backing member heat sealed to a polypropylene porous/permeable membrane to from a reservior therebetween. The patch can include a pharmaceutically acceptable adhesive (such as a acrylate adhesive) on the membrane layer to adhere the patch to the skin of the host, e.g., a mammal such as a human. A release liner such as a polyester release liner can also be provided to cover the adhesive layer prior to application of the patch to the skin as is conventional in the art. This patch assembly can be packaged in an aluminum foil or other suitable pouch again as is conventional in the art.

Alternatively, a compound of formula I or a salt thereof can be formulated into a "matrix-type" transdermal patch as in Examples J and K below. Drug Delivery Systems Characteristics and Biomedical Application, R. L Juliano, ed., Oxford University Press. N.Y. (1980); and Controlled Drug Delivery Vol. I Basic Concepts, Stephen D. Bruck (1983) described the theory and application of methods useful for transdermal delivery systems. The relevant teachings of these texts are herein incorporated by reference. The drug-matrix could be formed utilizing various polymers, e.g. silicone, polyvinyl alcohol, polyvinyl chloride-vinyl acetate copolymer. The "drug matrix" may then be packaged into an appropriate transdermal patch.

EXAMPLE J

| Patch | mg/g |
| --- | --- |
| Compound A | 200 |
| silicone polymer | 800 |

EXAMPLE K

| Patch | mg/g |
| --- | --- |
| Compound A | 300 |
| Polyvinyl chloride vinyl acetate co-polymer | 700 |

The invention also contemplates a package which contains a specific number of transdermal patches that may be utilized to complete a specified course of treatment. For example a package containing 7, 24 hour patches would be utilized to complete a one week course of therapy.

The relevant teachings of all published references cited herein as incorporated by reference.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

We claim:

1. A compound of the formula or a pharmaceutically acceptable salt thereof, wherein X represents Cl or F.

2. A compound defined in claim 1 in the form of the acetic acid salt.

3. A compound having the structural formula or a pharmaceutically acceptable salt thereof.

4. A compound having the structural formula or a pharmaceutically acceptable salt thereof.

5. An antihistaminic pharmaceutical composition which comprises an antihistaminic effective amount of a compound as defined in claim 1 in combination with a pharmaceutically acceptable carrier.

6. An antihistaminic pharmaceutical composition which comprises an antihistaminic effective amount of the compound defined in claim 2 in combination with a pharmaceutically acceptable carrier.

7. An antihistaminic pharmaceutical composition which comprises an antihistaminic effective amount of the compound defined in claim 3 in combination with a pharamaceutically acceptable carrier.

8. An antihistaminic pharmaceutical composition which comprises an antihistaminic effective amount of the compound defined in claim 4 in combination with a pharmaceutically acceptable carrier.

9. A composition as defined in claim 7 in unit dosage form.

10. A composition as defined in claim 8 in unit dosage form.

11. A transdermally acceptable pharmaceutical composition comprising an anti-allergic effective amount of a compound as defined in claim 1 and a pharamaceutically acceptable transdermal carrier.

12. A transdermally acceptable pharamaceutical composition comprising a anti-allergic effective amount of a compound as defined in claim 3 and a pharmaceutically acceptable transdermal carrier.

13. A transdermally acceptable pharmaceutical composition comprising an anti-allergic effective amount of a compound as defined in claim 4 and a pharmaceutically acceptable transdermal carrier.

14. A method for treating allergic reactions in a mammal which comprises administering to said mammal an anti-allergic effective amount of a compound as defined in claim 1.

15. A method of treating allergic reactions in a mammal which comprises administering to said mammal an anti-allergic effective amount of a compound as defined in claim 3.

16. A method for treating allergic reactions in a mammal which comprises administering to said mammal an anti-allergic effective amount of a compound as defined in claim 4.

* * * * *